(12) United States Patent
Dubail et al.

(10) Patent No.: US 11,638,521 B2
(45) Date of Patent: May 2, 2023

(54) METHODS AND SYSTEMS FOR DETERMINING A REFRACTION OF AT LEAST AN EYE OF A PERSON

(71) Applicant: Essilor International, Charenton-le-Pont (FR)

(72) Inventors: Marie Dubail, Charenton-le-Pont (FR); Anne-Catherine Scherlen, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 197 days.

(21) Appl. No.: 16/956,790

(22) PCT Filed: Dec. 4, 2018

(86) PCT No.: PCT/EP2018/083528
§ 371 (c)(1),
(2) Date: Jun. 22, 2020

(87) PCT Pub. No.: WO2019/120992
PCT Pub. Date: Jun. 27, 2019

(65) Prior Publication Data
US 2020/0315448 A1    Oct. 8, 2020

(30) Foreign Application Priority Data

Dec. 22, 2017 (EP) .................... 17306897

(51) Int. Cl.
*A61B 3/103* (2006.01)
*A61B 3/06* (2006.01)
(Continued)

(52) U.S. Cl.
CPC ............ *A61B 3/103* (2013.01); *A61B 3/0008* (2013.01); *A61B 3/066* (2013.01); *G02C 7/104* (2013.01); *G16H 50/50* (2018.01)

(58) Field of Classification Search
CPC .. A61B 3/14; A61B 3/12; A61B 3/102; A61B 3/0025; A61B 3/0008; A61B 3/113;
(Continued)

(56) References Cited

U.S. PATENT DOCUMENTS

| | | | |
|---|---|---|---|
| 5,467,151 A | 11/1995 | Kohayakawa | |
| 6,663,242 B1 | 12/2003 | Davenport | |

(Continued)

FOREIGN PATENT DOCUMENTS

| | | |
|---|---|---|
| EP | 3 056 939 A1 | 8/2016 |
| JP | H06-007298 A | 1/1994 |

(Continued)

OTHER PUBLICATIONS

International Search Report, PCT/EP2018/083528, dated Jun. 13, 2019.
(Continued)

*Primary Examiner* — Collin X Beatty
*Assistant Examiner* — Grant A Gagnon
(74) *Attorney, Agent, or Firm* — Nixon & Vanderhye

(57) ABSTRACT

Method for determining a refraction of at least an eye of a person under specific spectral conditions, the method including: an eye illumination step, during which the eye of the person is illuminated under the specific spectral conditions, the specific spectral conditions being provided by a polychromatic source having a spectrum which is different from the spectrum of a white light source and/or by a chromatic filter positioned before the eye of the person and illuminated by a source; and a refraction determination step during which the refraction of the eye of the person is determined under the specific spectral conditions.

20 Claims, 8 Drawing Sheets

(51) Int. Cl.
*A61B 3/00* (2006.01)
*G02C 7/10* (2006.01)
*G16H 50/50* (2018.01)

(58) Field of Classification Search
CPC ....... A61B 3/1015; A61B 3/103; A61B 3/107; A61B 3/10; A61B 3/152; A61B 3/1225; A61B 3/1005; A61B 3/1025; A61B 3/145; A61B 3/0091; A61B 3/112; A61B 3/117; A61B 5/14532; A61B 3/13; A61B 3/135; A61B 3/032; A61B 5/150022; A61B 5/0066; A61B 3/0041; A61B 5/150167; A61B 3/0058; A61B 5/15123; A61B 5/157; A61B 5/150152; A61B 5/150503; A61B 3/1241; A61B 5/150175; A61B 5/150358; A61B 3/0075; A61B 5/150572; A61B 3/132; A61B 3/1208; A61B 5/15151; A61B 3/156; A61B 5/15169; A61B 3/024; A61B 5/15153; A61B 5/15163; A61B 3/0033; A61B 5/15146; A61B 5/15171; A61B 5/15113; A61B 5/15178; A61B 3/0083; A61B 5/15186; A61B 5/14546; A61B 3/101; A61B 90/30; A61B 3/1233; A61B 5/150427; A61B 5/15117; A61B 3/1173; A61B 5/1455; A61B 5/163; A61B 3/028; A61B 5/150213; A61B 3/125; A61B 5/0059; A61B 5/150099; A61B 5/15184; A61B 90/20; A61B 5/15176; A61B 3/18; A61B 17/32093; A61B 5/15087; A61B 5/150221; A61B 5/150068; A61B 3/165; A61B 3/158; A61B 5/150824; A61B 5/151; A61B 3/063; A61B 5/398; A61B 3/1035; A61B 5/150412; A61B 5/14555; A61B 2090/306; A61B 3/08; A61B 5/0071; A61B 3/005; A61B 3/1216; A61B 3/066; A61B 3/06; A61B 5/6821; A61B 5/1411; A61B 5/150435; A61B 5/150809; A61B 5/15161; A61B 3/11; A61B 5/6803; A61B 8/10; A61B 3/022; A61B 3/15; A61B 5/0073; A61B 5/15019; A61B 3/00; A61B 5/150061; A61B 5/15107; A61B 5/7257; A61B 3/0285; A61B 3/111; A61B 3/1176; A61B 5/0075; A61B 5/150816; A61B 18/20; A61B 3/02; A61B 5/0084; A61B 5/150251; A61B 3/036; A61B 3/04; A61B 5/0013; A61B 5/0068; A61B 3/09; A61B 5/150916; A61B 5/6898; A61B 2090/309; A61B 5/0077; A61B 5/1427; A61B 5/1486; A61B 5/1513; A61B 18/2025; A61B 5/1171; A61B 5/15194; A61B 1/0684; A61B 5/16; A61B 5/0488; A61B 90/36; A61B 2017/00694; A61B 3/185; A61B 5/15182; A61B 1/07; A61B 3/085; A61B 3/16; A61B 1/0655; A61B 2018/00636; A61B 2090/502; A61B 2576/02; A61B 5/0002; A61B 5/0022; A61B 5/1103; A61B 5/150519; A61B 5/150664; A61B 5/1519; A61B 5/165; A61B 5/7267; A61B 5/7275; A61B 3/0016; A61B 3/154; A61B 5/01; A61B 5/0261; A61B 5/18; A61B 5/4863; A61B 5/7264; A61B 1/06; A61B 1/227; A61B 2017/00057; A61B 5/15174; A61B 5/161; A61B 5/6814; A61B 90/50; A61B 1/043; A61B 1/0669; A61B 2560/0431; A61B 5/150755; A61B 5/7203; A61B 5/1114; A61B 5/14558; A61B 5/378; A61B 1/0661; A61B 18/22; A61B 2018/20351; A61B 2560/0223; A61B 2562/0219; A61B 2576/00; A61B 5/0086; A61B 5/0095; A61B 5/02007; A61B 5/117; A61B 5/15111; A61B 5/7246; A61B 1/0638; A61B 1/303; A61B 2560/0425; A61B 5/0062; A61B 5/0088; A61B 5/11; A61B 5/14551; A61B 5/150083; A61B 5/150832; A61B 5/150954; A61B 5/162; A61B 5/4064; A61B 5/411; A61B 5/725; A61B 5/742; A61B 5/7445; A61B 1/00009; A61B 1/00172; A61B 2017/306; A61B 2090/3735; A61B 2503/22; A61B 2562/0204; A61B 2562/0242; A61B 5/0205; A61B 5/14865; A61B 5/4845; A61B 5/7207; A61B 90/361; A61B 1/128; A61B 2018/00642; A61B 2018/20355; A61B 2018/20359; A61B 2018/207; A61B 2090/049; A61B 2090/3937; A61B 2090/506; A61B 2560/0233; A61B 2560/0475; A61B 2562/0233; A61B 2562/0238; A61B 3/0066; A61B 5/004; A61B 5/021; A61B 5/12; A61B 5/145; A61B 5/150229; A61B 5/150259; A61B 5/150748; A61B 5/15128; A61B 5/168; A61B 5/24; A61B 5/6886; A61B 5/7405; A61B 8/4416; A61B 1/00006; A61B 1/00105; A61B 1/00142; A61B 1/00165; A61B 1/042; A61B 1/267; A61B 1/32; A61B 2562/0247; A61B 2562/043; A61B 5/0035; A61B 5/0082; A61B 5/1075; A61B 5/1079; A61B 5/1124; A61B 5/150343; A61B 5/361; A61B 5/369; A61B 5/377; A61B 5/4011; A61B 5/4023; A61B 5/416; A61B 5/42; A61B 5/4331; A61B 5/445; A61B 5/4842; A61B 5/486; A61B 5/6852; A61B 8/461; A61B 1/00057; A61B 1/00059; A61B 1/0008; A61B 1/00114; A61B 1/0607; A61B 18/203; A61B 2018/00452; A61B 201/20361; A61B 2018/2211; A61B 2090/061; A61B 2090/373; A61B 2503/10; A61B 2560/0214; A61B 2560/0242; A61B 2562/08; A61B 2562/166; A61B 3/0325; A61B 34/10; A61B 5/0064; A61B 5/024; A61B 5/53; A61B 5/14535; A61B 5/15016; A61B 5/150282; A61B 5/150305; A61B 5/15109; A61B 5/4255; A61B 5/4839; A61B 5/489; A61B 5/681; A61B 5/7282; A61B 5/7425; A61B 8/4472; A61B 90/04; A61B 90/39; A61B 1/000095; A61B 1/00034; A61B 1/00039; A61B 1/00096; A61B 1/00103; A61B 1/00126; A61B 1/00135; A61B 1/00137; A61B 1/0019; A61B 1/045; A61B 1/0653; A61B 1/24; A61B 1/31; A61B 1/313; A61B 17/00491; A61B 2017/00022; A61B 2017/00725; A61B 2018/00458; A61B 2018/00476; A61B 2018/00589; A61B 2018/00982; A61B 2090/3983; A61B
2560/0456; A61B 2562/0257; A61B
2562/0295; A61B 2562/12; A61B 34/20;
A61B 5/0042; A61B 5/055; A61B 5/107;
A61B 5/1072; A61B 5/1104; A61B
5/1128; A61B 5/14507; A61B 5/14552;
A61B 5/14553; A61B 5/14556; A61B
5/1468; A61B 5/150137; A61B 5/150511;
A61B 5/150946; A61B 5/15121; A61B
5/15142; A61B 5/15155; A61B 5/4076;
A61B 5/4094; A61B 5/412; A61B 5/441;
A61B 5/444; A61B 5/4821; A61B
5/4848; A61B 5/726; A61B 8/06; A61B
8/4483; A61B 90/37; A61B 1/00011;
A61B 1/00036; A61B 1/00042; A61B
1/00045; A61B 1/0005; A61B 1/00052;
A61B 1/0011; A61B 1/00167; A61B
1/00186; A61B 1/00188; A61B 1/00193;
A61B 1/002; A61B 1/046; A61B 1/05;
A61B 1/063; A61B 1/0676; A61B 1/233;
A61B 1/3132; A61B 17/0231; A61B
17/3421; A61B 18/201; A61B 18/24;
A61B 2017/00061; A61B 2017/00154;
A61B 2017/00716; A61B 2017/00876;
A61B 2018/00005; A61B 2018/00315;
A61B 2034/107; A61B 2034/2055; A61B
2034/2057; A61B 2050/0066; A61B
2090/062; A61B 2090/0814; A61B
2090/3612; A61B 2090/3616; A61B
2090/3618; A61B 2090/363; A61B
2090/372; A61B 2505/07; A61B
2560/0252; A61B 2560/0418; A61B
2560/0443; A61B 2560/0493; A61B
2562/0215; A61B 2562/146; A61B
2562/227; A61B 5/00; A61B 5/015;
A61B 5/02042; A61B 5/02216; A61B 5/02416;
A61B 5/0285; A61B 5/031; A61B 5/05;
A61B 5/0507; A61B 5/08; A61B 5/1032;
A61B 5/1116; A61B 5/1118; A61B
5/1172; A61B 5/1176; A61B 5/14539;
A61B 5/1459; A61B 5/15003; A61B
5/150091; A61B 5/150183; A61B
5/150267; A61B 5/150274; A61B
5/15029; A61B 5/150419; A61B
5/150702; A61B 5/15159; A61B 5/15192;
A61B 5/40; A61B 5/4082; A61B 5/443;
A61B 5/6824; A61B 5/6831; A61B
5/6848; A61B 5/72; A61B 5/721; A61B
5/7228; A61B 5/7239; A61B 5/7242;
A61B 5/7271; A61B 5/7278; A61B
5/7415; A61B 5/7455; A61B 5/7475;
A61B 50/30; A61B 6/463; A61B 6/469;
A61B 6/506; A61B 8/4209; A61B 8/463;
A61B 8/5261; A61B 8/56; A61B
1/000094; A61B 1/00022; A61B 1/0004;
A61B 1/00062; A61B 1/00073; A61B
1/00082; A61B 1/00097; A61B 1/00133;
A61B 1/00149; A61B 1/0016; A61B
1/00163; A61B 1/00177; A61B 1/00183;
A61B 1/0057; A61B 1/018; A61B 1/04;
A61B 1/041; A61B 1/044; A61B 1/0615;
A61B 1/0646; A61B 1/0692; A61B
10/00; A61B 13/00; A61B 17/00; A61B
17/02; A61B 17/04; A61B 17/0469; A61B
17/11; A61B 17/30; A61B 17/32; A61B
17/32053; A61B 17/34; A61B 17/3417;
A61B 17/8863; A61B 18/12; A61B
18/14; A61B 18/1485; A61B 18/18; A61B
18/245; A61B 18/26; A61B 2017/00044;
A61B 2017/00066; A61B 2017/00084;
A61B 2017/00106; A61B 2017/00194;
A61B 2017/00199; A61B 2017/00225;
A61B 2017/0023; A61B 2017/00438;
A61B 2017/00477; A61B 2017/00707;
A61B 2017/00734; A61B 2017/00756;
A61B 2017/0862; A61B 2017/00902;
A61B 2017/00946; A61B 2017/00951;
A61B 2017/00973; A61B 2017/22051;
A61B 2017/22059; A61B 2017/22087;
A61B 2017/3437; A61B 2017/3452;
A61B 2018/005; A61B 2018/00577;
A61B 2018/00601; A61B 2018/00607;
A61B 2018/00738; A61B 2018/00755;
A61B 2018/00875; A61B 2018/00916;
A61B 2018/00994; A61B 2018/126;
A61B 2018/1412; A61B 2018/1425;
A61B 2018/202; A61B 2018/2035; A61B
2018/204; A61B 2018/2075; A61B
2018/208; A61B 2018/2205; A61B
2018/2244; A61B 2018/2253; A61B
2018/2261; A61B 2018/2294; A61B
2034/102; A61B 2034/105; A61B
2034/2051; A61B 2034/2065; A61B
2034/2072; A61B 2034/256; A61B
2034/742; A61B 2050/005; A61B
2050/0051; A61B 2050/0054; A61B
2050/0084; A61B 2050/0086; A61B
2050/3008; A61B 2050/3009; A61B
2050/3015; A61B 2050/311; A61B
2090/036; A61B 2090/065; A61B
2090/308; A61B 2090/371; A61B
2090/374; A61B 2090/3945; A61B
2090/3979; A61B 2218/005; A61B
2503/06; A61B 2503/08; A61B 2503/20;
A61B 2503/40; A61B 2560/0238; A61B
2560/0271; A61B 2560/0276; A61B
2560/04; A61B 2560/0406; A61B
2562/02; A61B 2562/0209; A61B
2562/0214; A61B 2562/0223; A61B
2562/028; A61B 2562/04; A61B
2562/223; A61B 2576/026; A61B 34/25;
A61B 34/30; A61B 34/35; A61B 34/70;
A61B 34/75; A61B 46/10; A61B 5/0004;
A61B 5/0008; A61B 5/0015; A61B
5/0036; A61B 5/0037; A61B 5/0053;
A61B 5/0091; A61B 5/02055; A61B
5/02438; A61B 5/02444; A61B 5/025;
A61B 5/026; A61B 5/0265; A61B
5/0275; A61B 5/06; A61B 5/066; A61B
5/103; A61B 5/1036; A61B 5/1071; A61B
5/1076; A61B 5/1077; A61B 5/1101;
A61B 5/1105; A61B 5/1112; A61B
5/1121; A61B 5/1127; A61B 5/14542;
A61B 5/1495; A61B 5/150053; A61B
5/150106; A61B 5/150312; A61B
5/150374; A61B 5/150389; A61B
5/15045; A61B 5/150534; A61B
5/150541; A61B 5/150961; A61B
5/15101; A61B 5/15115; A61B 5/15125;
A61B 5/15126; A61B 5/15132; A61B 5/15136; A61B 5/15149; A61B 5/15165; A61B 5/1518; A61B 5/155; A61B 5/291; A61B 5/296; A61B 5/339; A61B 5/349; A61B 5/352; A61B 5/389; A61B 5/4035; A61B 5/4261; A61B 5/442; A61B 5/446; A61B 5/4519; A61B 5/4547; A61B 5/4812; A61B 5/4836; A61B 5/4851; A61B 5/4857; A61B 5/4875; A61B 5/4878; A61B 5/6802; A61B 5/6817; A61B 5/682; A61B 5/6826; A61B 5/6833; A61B 5/6843; A61B 5/6876; A61B 5/6887; A61B 5/6896; A61B 5/706; A61B 5/7221; A61B 5/7225; A61B 5/7285; A61B 5/743; A61B 5/748; A61B 5/7485; A61B 5/749; A61B 50/10; A61B 50/13; A61B 50/20; A61B 50/22; A61B 50/3001; A61B 50/31; A61B 6/00; A61B 6/03; A61B 6/4233; A61B 6/465; A61B 6/467; A61B 6/488; A61B 6/507; A61B 6/508; A61B 6/542; A61B 8/00; A61B 8/0858; A61B 8/13; A61B 8/14; A61B 8/4281; A61B 8/4427; A61B 8/4494; A61B 8/467; A61B 8/52; A61B 8/5238; A61B 90/00; A61B 90/06; A61B 90/14; A61B 90/53; A61B 90/57; A61B 90/60; A61B 90/70; A61B 90/98; G16H 50/20; G16H 30/40; G16H 40/67; G16H 40/63; G16H 15/00; G16H 30/20; G16H 50/30; G16H 10/60; G16H 50/50; G16H 50/70; G16H 20/10; G16H 20/17; G16H 10/40; G16H 20/40; G16H 40/20; G16H 70/20; G16H 80/00; G16H 20/60; G16H 20/00; G16H 20/70; G16H 20/13; G16H 20/30; G16H 40/40; G16H 40/60; G02C 7/04; G02C 7/02; G02C 7/027; G02C 2202/22; G02C 7/028; G02C 11/10; G02C 2202/24; G02C 7/047; G02C 13/005; G02C 7/083; G02C 2202/20; G02C 7/06; G02C 2202/16; G02C 7/042; G02C 7/061; G02C 13/003; G02C 7/049; G02C 7/101; G02C 2202/10; G02C 2202/12; G02C 2202/14; G02C 7/044; G02C 11/04; G02C 7/024; G02C 7/086; G02C 7/088; G02C 7/022; G02C 2202/06; G02C 7/045; G02C 7/08; G02C 2202/18; G02C 7/025; G02C 7/041; G02C 7/048; G02C 7/066; G02C 7/081; G02C 13/001; G02C 7/102; G02C 7/104; G02C 7/12; G02C 11/00; G02C 7/021; G02C 7/085; G02C 7/10; G02C 9/00; G02C 1/06; G02C 2200/02; G02C 2200/08; G02C 2202/04; G02C 3/003; G02C 7/00; G02C 7/063; G02C 7/105; G02C 7/108; G02C 9/02; G02C 1/023; G02C 11/06; G02C 11/08; G02C 13/00; G02C 2202/02; G02C 2202/08; G02C 30/02; G02C 5/001; G02C 5/08; G02C 7/043; G02C 7/046; G02C 7/107; G02C 7/14; G02C 7/16

See application file for complete search history.

(56) References Cited

U.S. PATENT DOCUMENTS

| | | | |
|---|---|---|---|
| 2007/0002444 | A1 | 1/2007 | Piers et al. |
| 2015/0002810 | A1 | 1/2015 | Altheimer et al. |
| 2016/0242670 | A1 | 8/2016 | Suzuki et al. |
| 2017/0095147 | A1 | 4/2017 | Copland et al. |

FOREIGN PATENT DOCUMENTS

| | | |
|---|---|---|
| JP | 2015-506499 A | 3/2015 |
| WO | WO 2011/130314 | 10/2011 |
| WO | WO2012/135661 | 10/2012 |
| WO | 2015/053210 A1 | 4/2015 |
| WO | WO2015/168794 | 11/2015 |
| WO | WO 2016/145064 | 9/2016 |

OTHER PUBLICATIONS

Office Action issued in Japanese Patent Application No. 2020-534922 dated Oct. 17, 2022.

METHODS AND SYSTEMS FOR DETERMINING A REFRACTION OF AT LEAST AN EYE OF A PERSON

FIELD OF THE INVENTION

The invention relates to methods and systems for determining a refraction of at least an eye of a person, to methods and systems for compensating a refraction of an eye of a person and to methods and systems for selecting a chromatic filter for an optical system adapted for a person.

BACKGROUND OF THE INVENTION

When an eye is illuminated by polychromatic visible light, the different wavelengths of visible light focus in different plans, either behind (long wavelength) or in front (short wavelength) of the retina plan. The amplitude of this defocus is known as longitudinal chromatic aberration.

Colored filters are more and more used nowadays in eyewear, not only for sunglasses, but also in order to improve comfort and vision in various light conditions, such as night or glare or to take into account a transition between different light conditions.

However, colored filters alter the spectrum of incoming light and thus may induce ametropic shift and decrease the comfort or the quality of vision.

For example, at a luminance level of 10 candela per square meter ($cd/m^2$), high-pass band filter (i.e. that filter signals with a wavelength superior or equal to 600 nm) induces in average an hyperopic shift of 0.2 dioptries (D), and low-pass band filter (i.e. that filter signals with a wavelength inferior or equal to 500 nm) induces in average a myopic shift of −0.8 D. The hyperopic shift can reach 0.4 D for myopes and the myopic shift can reach −1.2 D. The change of refraction is larger on myopes compared to hypermetropes.

The ametropic shift resulting from polychromatic filters can induce fatigue and reduce visual performances (visual acuity, contrast sensitivity, reading speed . . . ).

Moreover, when determining eyewear adapted for a person, the prescription of the wearer is often taken into account, however the prescription corresponds to standard spectral conditions. Therefore, the refraction induced by the eyewear is not adapted to specific non-standard spectral conditions.

Therefore, there is a need to methods and systems that would allow, according to spectral features of the light surrounding the eye of a person, determining a refraction of at least an eye of a person, compensating a refraction of an eye of a person and selecting a chromatic filter for an optical system adapted for a person.

One object of the present invention is to provide such methods and systems.

SUMMARY OF THE INVENTION

To this end, the invention proposes a method for determining a refraction of at least an eye of a person under specific spectral conditions, the method comprising:
  an eye illumination step, during which the eye of the person is illuminated under said specific spectral conditions, said specific spectral conditions being provided by a polychromatic source having a spectrum which is different from the spectrum of a white light source and/or by a chromatic filter positioned before the eye of the person and illuminated by a source, and
  a refraction determination step during which the refraction of the eye of the person is determined under said specific spectral conditions.

Measuring the refractive error of the wearer with the specific spectral conditions allows producing an adapted prescription in order to better focus the light on the retina. The wearer will have a sharper vision and produce less accommodative effort.

Indeed, wearing a low pass band filter instead of a neutral density filter under the same luminance level of 10 $cd/m^2$, induces on average a loss of two lines of visual acuity. The average visual acuity of a panel of thirty healthy people under maximum contrast and a luminance level of 10 $cd/m^2$ is −0.15 log when the incoming light is filtered by a filter of neutral density and 10% transmission, and +0.12 D when the incoming light is instead filtered by a low pass band filter having a cutting value of 500 nm and 10% transmission.

Advantageously, the invention allows gathering data relevant for the subsequent determination of an optical system adapted for a wearer under specific spectral conditions. Indeed, the invention determines a refraction of at least an eye of a person under specific spectral conditions.

According to further embodiments of the method according to the invention,
  the polychromatic source has a spectrum whose at least one chromatic coordinates x or y in the CIE xyY color space differs from the corresponding chromatic coordinates of the black body loci by at least 0.01, preferably by at least 0.02, advantageously by at least 0.03; and/or
  the chromatic filter has a chroma value strictly superior to 10, preferably strictly superior to 20, advantageously strictly superior to 30; and/or
  the refraction is determined by using a duochrome test, the colors of the duochrome test being chosen as a function of the specific spectral conditions.

Another object of the invention is a method for determining a spectral-refraction model adapted to a person, the method comprising:
  a specific spectral conditions providing step, during which a plurality of specific spectral conditions are provided,
  a spectral parameter providing step, during which for each of the specific spectral conditions, at least one spectral parameter, such as the spectrum or the light intensity, related to said specific spectral conditions is provided,
  a refraction determination step, during which a refraction of the eye of the person is successively determined for each of the specific spectral conditions according to a method for determining a refraction of at least an eye of a person under specific spectral conditions according to the invention, and
  a spectral-refraction model determining step, during which a model of the refraction of the eye of the person as a function of the spectral parameter is determined based on each of the refractions of the eye of the person and on each of the spectral parameters.

Advantageously, the invention allows establishing a relationship between a spectral parameter and a refraction of an eye of a person.

According to further embodiments of the method according to the invention, during the spectral-refraction model determining step, the model is determined by interpolating and/or extrapolating the refraction of the eye of the person as a function of the spectral parameter.

Another object of the invention is a method for determining a refraction of at least an eye of a person under specific spectral conditions, the method comprising:

a spectral-refraction model providing step, during which a model of a refraction of at least an eye as a function of a spectral parameter is provided, a spectral parameter providing step, during which at least one spectral parameter related to specific spectral conditions of the person is provided, and a refraction determination step, during which a refraction of the eye of the person under specific light conditions is determined based on the model and on the light parameter.

Such a method allows to predict the refractive error induced by specific spectral conditions and to compensate it without a measurement. The result is generic rather than adapted to individuals. Such method is useful especially for sunlenses for emmetropes.

Advantageously, the invention allows determining a refraction of an eye of a person remotely and without instrumentation.

According to further embodiments of the method according to the invention, during the spectral-refraction model providing step, the model of a refraction of at least an eye as a function of a spectral parameter is determined according to a method for determining a spectral-refraction model adapted to a person according to the invention.

Another object of the invention is a method for compensating a refraction of an eye of a person under wearing spectral conditions with an optical system comprising a component configured so as to refract light before the eye of the person, the method comprising:

a refraction determination step, during which a refraction of the eye of the person under specific spectral conditions is determined according to a method for determining a refraction of at least an eye of a person under specific spectral conditions according to the invention, an optical system providing step, during which an optical system is provided, the optical system comprising a component configured so as to refract light before the eye of the person, the component being chosen as a function of the determined refraction, and a refraction compensation step, during which the refraction of the eye of the person under wearing spectral conditions is compensated by the component of the optical system.

Advantageously, the invention allows compensating for longitudinal chromatic aberration corresponding to the wearing spectral conditions.

According to further embodiments of the method according to the invention, during the refraction determination step, the specific spectral conditions are sensibly similar to the wearing spectral conditions.

Another object of the invention is a method for selecting a chromatic filter for an optical system adapted for a person among a plurality of chromatic filters, the method comprising:

a target refraction providing step, during which a target refraction, such as the prescription of the person, is provided, an ophthalmic lens providing step, during which an ophthalmic lens is provided, the ophthalmic lens being associated with a refraction, a chromatic filter providing step, during which a plurality of chromatic filters are provided, each chromatic filter being associated with a refraction determined according to a method for determining a refraction of at least an eye of a person under specific spectral conditions according to the invention, a resultant refraction determination step, during which, for each of the chromatic filters, the refraction resulting of the association of the ophthalmic lens and the chromatic filter is determined, a refraction difference determination step, during which a difference between the resultant refraction and the target refraction is determined for each chromatic filter, and a chromatic filter selection step during which the chromatic filter inducing the least difference between the resultant refraction and the target refraction is selected.

Advantageously, the invention allows selecting a chromatic filter adapted to a person under specific spectral conditions.

Another object of the invention is a system adapted to determine the refraction of at least an eye of a person under specific spectral conditions, the system comprising:

a light source adapted to illuminate the eye of the person under specific spectral conditions, the specific spectral conditions being provided by a polychromatic source having a spectrum which is different from the spectrum of a white light and/or by a chromatic filter positioned before the eye of the person and illuminated by a source, and a refraction determining device adapted to determine the refraction of the eye of the person.

Advantageously, the invention allows determining the refraction of at least an eye of a person under specific spectral conditions.

Another object of the invention is an optical system adapted for a person, the optical system comprising a component configured so as to refract light before the eye of the person, the optical system being adapted to compensate a refraction of the eye of the person under wearing spectral conditions.

Advantageously, the invention allows compensating a refraction of the eye of the person under wearing spectral conditions.

Another object of the invention is an optical system adapted for a person, the optical system comprising a chromatic filter selected among a plurality of chromatic filters.

Advantageously, the invention allows selecting a chromatic filter adapted to a person under specific spectral conditions.

BRIEF DESCRIPTION OF THE DRAWINGS

Non limiting embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION OF THE DRAWINGS

Figure 1:
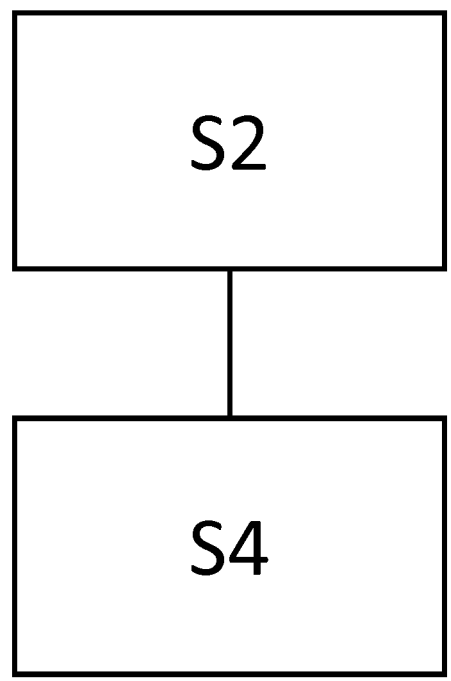
FIG. 1 is a schematic diagram of the steps of a method for determining a refraction of at least an eye of a person according to an embodiment of the invention.

The invention relates to a method for determining a refraction of at least an eye 2 of a person under specific spectral conditions, as illustrated on FIG. 1.

In the sense of the invention, the determined refraction refers to the change in direction of wave propagation of visible light through an eye of the person. The determined refraction may correspond to an emmetropic or to an ametropic eye, referring to any eye defect such as myopia, hypermetropia, presbyopia, astigmatism and the like.

In the sense of the invention, the determined refraction may be monocular or binocular.

In the sense of the invention, the specific spectral conditions are spectral conditions which differ from that of CIE Standard Illuminant D65. The specific spectral conditions may include conditions related to chromaticity, such as the wavelength distribution, and/or conditions related to total light intensity.

The method comprises an eye illumination step S2, and a refraction determination step S4.

Figure 6:
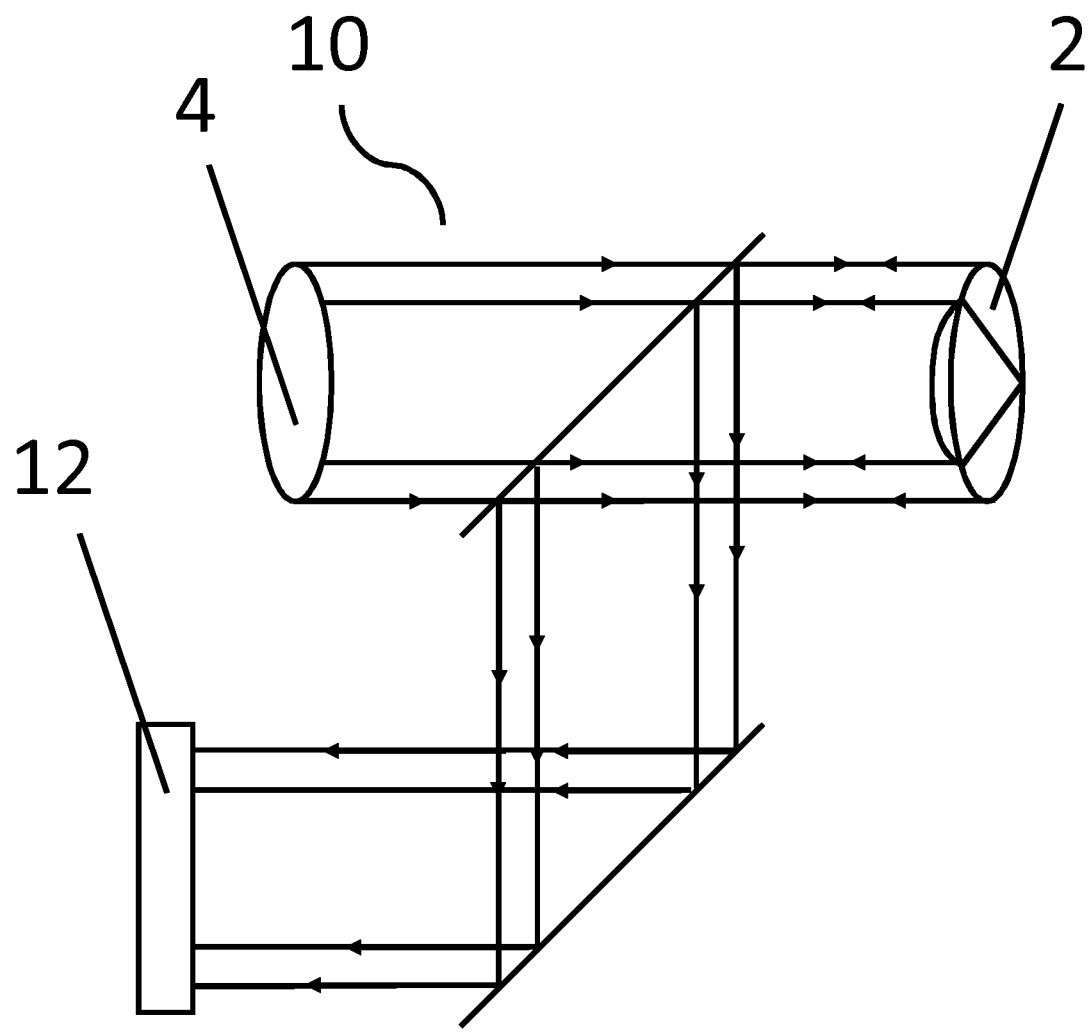
FIG. 6 is a schematic diagram of a system adapted to determine the refraction of at least an eye of a person according to an embodiment of the invention.

During the eye illumination step S2, at least one eye 2 of the person is illuminated by a light source 4 under said specific spectral conditions as illustrated on FIG. 6.

The specific spectral conditions may be homogenous in space and/or time. In other words, the difference between the maximum and minimum hue of the light illuminating the at least one eye 2 of the person is lower than 90°, preferably lower than 45°.

In a variant, the specific spectral conditions are not homogeneous in space and/or time. For example, such spectral conditions are obtained by sources which are spatially reduced (punctual) and/or dynamic.

The light source 4 may be a primary or a secondary light source. The light source 4 may illuminate the at least one eye 2 of the person directly or indirectly, for example by being reflected by a mirror.

The light source 4 may be a polychromatic source 6 having an emission spectrum which is different from the spectrum of a white light source. In this case, the specific spectral conditions are related to the emission spectrum of the polychromatic source 6.

Advantageously, no chromatic filter is required to generate specific spectral conditions, resulting in a simpler setup.

The light source 4 may be generated by one or more RGB light sources, for example by an RGB LED consisting of one red, one green, and one blue LED, or by a display monitor comprising such RGB LEDs.

Advantageously, RGB light sources may be used to fine-tune the specific spectral conditions. RGB light sources may also generate a plurality of light sources, each corresponding to different specific spectral conditions, and the method of the invention may be performed successively for each specific spectral condition.

The polychromatic source 6 may have a spectrum which at least one chromatic coordinates x or y in the CIE xyY color space differs from the corresponding chromatic coordinates of the black body loci by at least 0.01, preferably by at least 0.02, advantageously by at least 0.03.

A chromatic filter 8 may be positioned between at least one eye 2 of the person and the light source 4. The light source 4 is for example a CIE normalized source. Thus, the light emitted by the light source 4 is transmitted through the chromatic filter 8 and the transmitted light illuminates said at least one eye 2 of the person.

Advantageously, the specific spectral conditions may be obtained from any kind of light source 4.

The specific spectral conditions thus correspond to the transmission spectrum of the chromatic filter 8 illuminated by the light source 4.

The chroma value of the chromatic filter 8 may be calculated based on CIE 2° standard observer under CIE Standard Illuminant D65.

According to an embodiment of the invention, the chroma value of the chromatic filter 8 may be superior or equal to 10, preferably superior or equal to 20, and more preferably superior or equal to 30.

Advantageously, the chromatic filter 8 transmits light having a color noticeably different from white. Thus, the spectral transmission of the filter is different from a neutral filter whose transmittance would be identical from 400 nm to 800 nm.

During the refraction determination step S4, the refraction of said at least one eye 2 of the person is determined under said specific spectral conditions.

Advantageously, the invention allows determining data relevant for the subsequent determination of an optical system adapted for a wearer under specific spectral conditions.

The refraction determination step may be performed in an objective or in a subjective manner.

In other words, the refraction of said at least one eye 2 of the person may be determined based on a measurement performed by a measuring instrument such as a retinoscope or an auto-refractor corresponding to the objective manner.

Advantageously, the refraction may be determined even if the person cannot speak (e.g. a baby) or does not speak the language of the practitioner determining the refraction.

Alternatively, the refraction of said at least one eye 2 of the person may be determined based on feedback provided by the person, such as by an examination using a phoropter corresponding to the subjective manner.

Advantageously, subjective feedback is provided on which settings give the best vision.

In a variant or in addition, the refraction may be determined using a duochrome test or a multichrome test (color combinations) on an acuity test or an image to optimize the refraction. A duochrome test is a test commonly used to refine the final sphere in refraction, which makes use of the chromatic aberration of the eye. Indeed, because of the chromatic aberration of the eye, the shorter wavelengths (green) are focused in front of the longer wavelengths (red). Typically, the patient is asked to compare the clarity of letters on the green and on the red side of a panel. If the letters on the green side are clearer +0.25 D sphere power is added and if the letters on the red side are clearer −0.25 D sphere power is added. With optimal spherical correction, the letters on the red and green halves of the chart appear equally clear. Hence, the best refraction is defined by adapting the power of lenses until acuity or perception quality of letters are the same between red (650 nm) and green (500 nm) background. The suitable power of lenses allows to locate the retina focalisation in the half path of the defocalisation between green/red.

Advantageously, the color duochrome combination is chosen as a function of the filter spectrum to evaluate or as a function of the light source. For example, if a yellow filter (480 nm) is selected, the duochrome test is set, for example, with blue (420 nm) and yellow/green (540 nm) wavelengths to assess the new refraction. Preferably, the color combination covers and is centered on the cutting filter. The higher the range between the center and the extremity of the panel is, the higher the assessment precision is.

Figure 2:
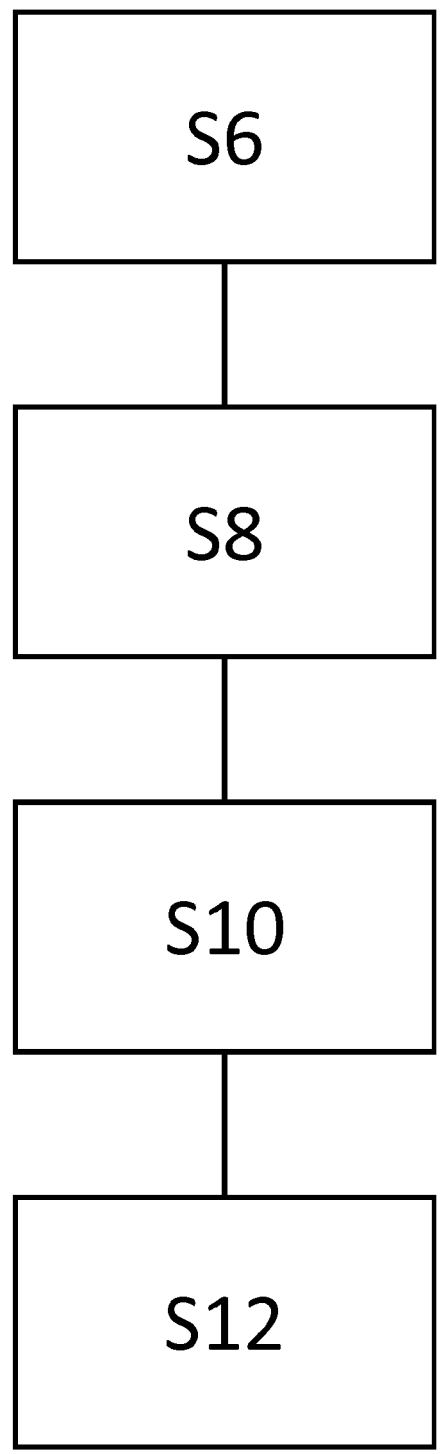
FIG. 2 is a schematic diagram of the steps of a method for determining a spectral-refraction model adapted to a person according to an embodiment of the invention.

Another object of the invention is a method for determining a spectral-refraction model adapted to a person, as illustrated on FIG. 2.

The method comprises a specific spectral conditions providing step S6, a spectral parameter providing step S8, a refraction determination step S10, and a spectral-refraction model determining step S12.

During the specific spectral conditions providing step S6, a plurality of specific spectral conditions are provided.

During the spectral parameter providing step S8, for each of the specific spectral conditions provided in the specific spectral conditions providing step S6, at least one spectral parameter related to said specific spectral conditions is provided. Such spectral parameter may include the spectrum or the light intensity.

During the refraction determination step S10, a refraction of at least one eye 2 of the person is successively determined for each of the specific spectral conditions. Each determination of the refraction of the at least one eye 2 of the person may be performed by a method comprising an eye illumination step S2, and a refraction determination step S4 according to the invention.

During the spectral-refraction model determining step S12, a model of the refraction of the eye of the person as a function of the spectral parameter is determined based on each of the refractions of the eye of the person determined during the refraction determination step S10 and on each of the spectral parameters provided during the spectral parameter providing step S8.

Advantageously a correspondence is established between each spectral parameter and each determined refraction. Therefore, the model may be used either to determine a refraction based on a spectral parameter or to determine a spectral parameter based on a refraction, The model may be determined by interpolating and/or extrapolating the refraction of the eye of the person as a function of the spectral parameter.

For example, the model is determined by a regression such as a least squares regression.

Advantageously, the model fits the spectral parameters and the determined refractions and is extended to any specific spectral conditions in a given range.

Figure 3:
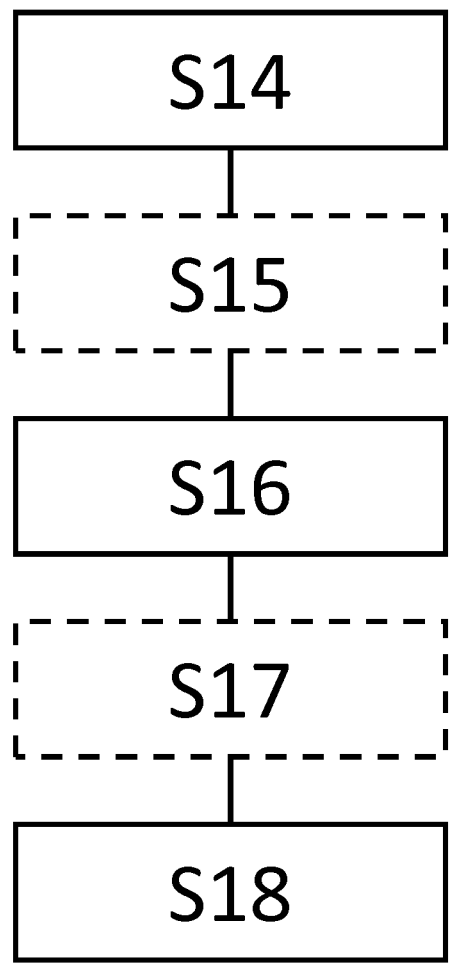
FIG. 3 is a schematic diagram of the steps of a method for determining a refraction of at least an eye of a person according to an embodiment of the invention.

Another object of the invention is a method for determining a refraction of at least an eye of a person under specific spectral conditions, as illustrated on FIG. 3.

The method comprises a spectral parameter providing step S14, a spectral-refraction model providing step S16 and a refraction determination step S18.

During the spectral parameter providing step S14, at least one spectral parameter related to the specific spectral conditions is provided.

During the spectral-refraction model providing step S16, a model of a refraction of at least an eye as a function of a spectral parameter, such as spectrum or light intensity, is provided.

The model may be previously determined by a method according to the invention, comprising a specific spectral conditions providing step S6, a spectral parameter providing step S8, a refraction determination step S10, and a spectral-refraction model determining step S12 as described here.

The model may be either generic or specific to a person or a category of people. In the sense of the invention, a category of people is for example an age or an eyesight category.

A plurality of specific models may be provided.

Advantageously, once a sufficient number of determinations of the refraction of an eye of a person is performed in order to establish the model, then the invention allows quick determination and without any instrumentation of other refractions, for example the refraction of the same eye under different spectral conditions, or the refraction of the eyes of many people belonging to the same category under any spectral conditions.

As an example, the model is a mathematical model. The model is, for example, determined using extreme filters (such as low pass-band (500 nm) and high pass band (600 nm) filters). The refraction defocus is obtained through the following expression:

$$D = a * \log\left(\frac{\frac{\int_{\lambda_1}^{\lambda_2} T(\lambda) \cdot d(\lambda)}{\lambda_2 - \lambda_1}}{\frac{\int_{\lambda_3}^{\lambda_4} T(\lambda) \cdot d(\lambda)}{\lambda_4 - \lambda_3}}\right) + b \qquad (1)$$

Where:

D is the refraction defocus, $T(\lambda)$ is the function of spectral transmission of the filter, $\lambda$ is the wavelength in nm, $$\frac{\int_{\lambda_1}^{\lambda_2} T(\lambda) \cdot d(\lambda)}{\lambda_2 - \lambda_1}$$

is the mean of the function between $\lambda_1$ and $\lambda_2$ (as an example between 480 nm and 580 nm), $$\frac{\int_{\lambda_3}^{\lambda_4} T(\lambda) \cdot d(\lambda)}{\lambda_4 - \lambda_3}$$

is the mean of the function between $\lambda_3$ and $\lambda_4$ (as an example between 580 nm and 680 nm), and a and b are constants.

As an alternative to equation (1), if the defocus $D_i(\lambda_i)$ is known for different wavelengths (at least two), and if the transmission $T_i(\lambda_i)$ of the filter that the wearer will have on his lens is also known, it is then possible to calculate the defocus needed to compensate the defocus of the filter using the following expression:

$$D_{final} = \frac{\sum_{i=1}^{N}(D_i(\lambda_i) * T_i(\lambda_i))}{\sum_{i=1}^{N}(T_i(\lambda_i))} \quad (2)$$

Where:

$D_{final}$ is the final refraction defocus, $D_i$ is the defocus induced by wavelength $\lambda_i$, $T_i$ is the transmission of the lens for $\lambda_i$, $\lambda_i$ is the wavelength expressed in nanometers and is comprised between 400 nm and 800 nm, and N is superior to 5.

The model may also integrate a luminance component because the defocus depends also on luminance. Hence, it is for instance possible to use three different models, one for scotopic, one for mesopic and one for photopic level.

It also possible to use two or more different models each model being adapted to a different photopic luminance level. Such examples of luminance levels may correspond to different ranges of luminance magnitude, for instance respectively below and above 1 cd/m², or may be referred to as respectively dark or scotopic light below 0.1 cd/m², mesopic light above 0.1 cd/m² and below 10 cd/m², and photopic light above 10 cd/m².

Age and ametropia may also be integrated in such a model.

During the refraction determination step S18, a refraction of the eye of the person under the specific spectral conditions is determined based on the provided model and on the provided spectral parameter.

The method of the invention may further comprise a personal parameter providing step S15, during which a personal parameter related to the person, such as related to the age or to the eyesight of the person, is provided.

In embodiments, the method further comprises a model selection step S17, during which a specific spectral-refraction model is selected among a plurality of provided models. Then, during the refraction determination step S18, the refraction of the eye of the person is determined based on the selected model. The selection of the model may be based on the provided personal parameter and/or based on the spectral parameter.

Advantageously, the model most adapted to the person and/or to the spectral conditions of interest is selected.

Figure 4:
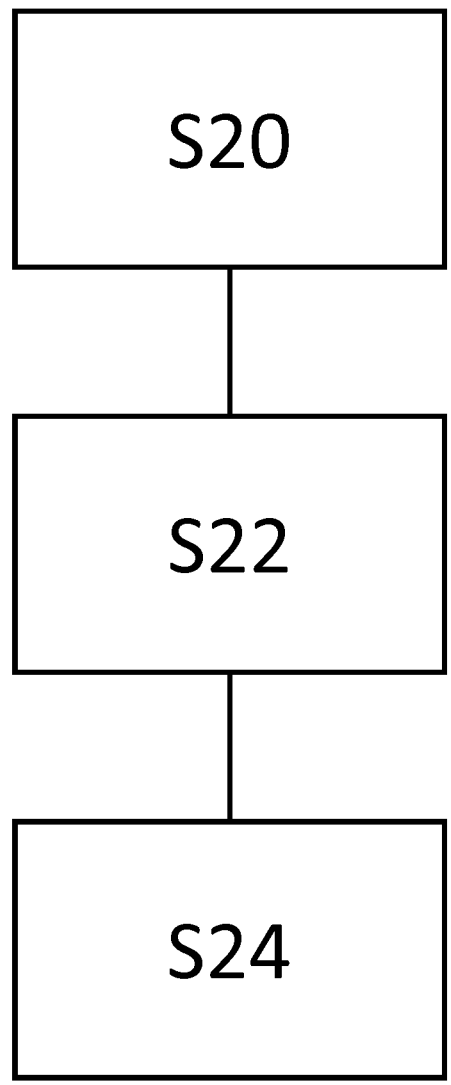
FIG. 4 is a schematic diagram of the steps of a method for compensating a refraction of an eye of a person according to an embodiment of the invention.

Another object of the invention is a method for compensating a refraction of an eye of a person under wearing spectral conditions with an optical system comprising at least one component configured so as to refract light before the eye of the person, as illustrated on FIG. 4.

Advantageously, the invention allows compensating the refraction of the eye of the person under wearing spectral conditions. Therefore, an optical system adapted to the person under the wearing spectral conditions may be provided.

The component may comprise a chromatic filter. The chromatic filter may be monochromatic or polychromatic. The optical filter may be active or passive. The optical filter may be uniform or may have a gradient.

For example, the spectrum of the optical filter is measured by using a spectrophotometer equipped with a full spectrum Xenon light source and a monochromator measuring light at least in the visible range (ex: 400 nm-800 nm).

The component may comprise an optical lens.

The method comprises a refraction determination step S20, an optical system providing step S22 and a refraction compensation step S24.

During the refraction determination step S20, a refraction of the eye of the person under specific spectral conditions is determined by a method.

Said method for determining a refraction of at least an eye of a person under specific spectral conditions may be a method according to the invention comprising an eye illumination step S2, and a refraction determination step S4.

Said method for determining a refraction of at least an eye of a person under specific spectral conditions may be a method according to the invention comprising a spectral parameter providing step S14, a spectral-refraction model providing step S16 and a refraction determination step S18.

The specific spectral conditions may be sensibly similar to the wearing spectral conditions.

During the optical system providing step S22, an optical system is provided. The optical system comprises one or more components, configured so as to refract light before the eye of the person.

The component is chosen as a function of the determined refraction.

Each component may be active or passive.

An active component is particularly advantageous in that it may be programmed to compensate for the wearing spectral conditions which may vary in time.

During the refraction compensation step S24, the refraction of the eye of the person under wearing spectral conditions is compensated by the component of the optical system.

As an example, refraction of the lenses of the wearer are adapted according to the filter parameters (transmission and spectrum) which has been chosen by the wearer. For instance, let's consider a person having for one eye a prescription of −2.00 D for myopia correction, for a visual acuity of 0 Log, also referred to as 10/10 visual acuity. Additionally, the person selects eyewear with a brown filter with 18% transmission. The combination of the lenses and the brown filter induces a visual acuity loss, the acuity is now 0.1 log (8/10). After performing a refraction determination step with the same filter in high luminance conditions, above 100 cd/m², we may obtain a refraction corresponding to −1.75 D, in order to achieve 10/10 visual acuity. Hence, in this example, during the refraction compensation step, the refraction of the eye of the person under wearing spectral conditions is compensated by the brown filter associated with a lens which final sun filter prescription is −1.75 D.

Figure 5:
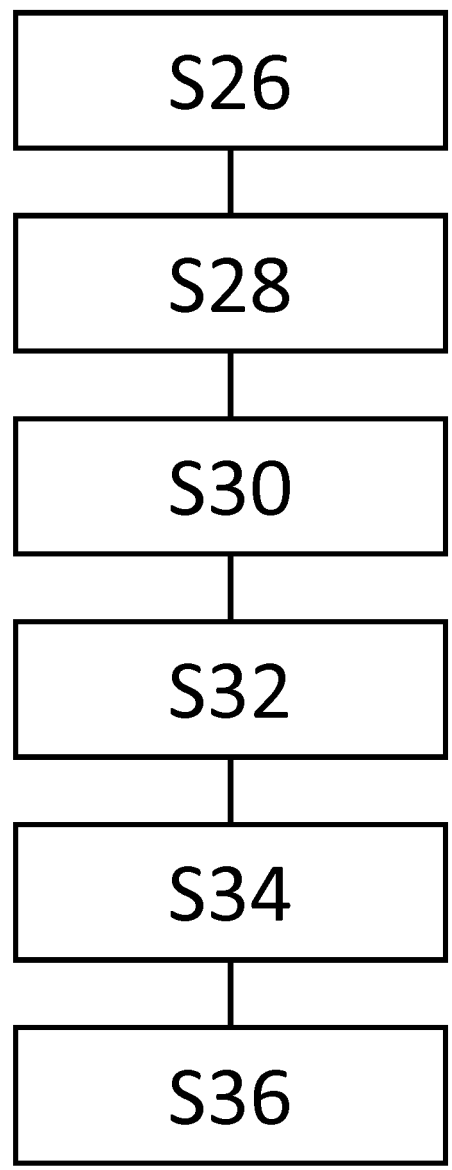
FIG. 5 is a schematic diagram of the steps of a method for selecting a chromatic filter for an optical system adapted for a person according to an embodiment of the invention.

Another object of the invention is a method for selecting a chromatic filter for an optical system adapted for a person among a plurality of chromatic filters, as illustrated on FIG. 5.

The method comprises a target refraction providing step S26, an ophthalmic lens providing step S28, a chromatic filter providing step S30, a resultant refraction determination step S32, a refraction difference determination step S34, and a chromatic filter selection step S36.

During the target refraction providing step S26, a target refraction, such as the prescription of the person, is provided. In embodiments, the target refraction may correspond to an emmetropic eye.

During the ophthalmic lens providing step S28, an ophthalmic lens is provided. The ophthalmic lens is associated with a refraction.

During the chromatic filter providing step S30, a plurality of chromatic filters are provided.

Each chromatic filter is associated with a refraction. The refraction may be previously determined according to a method for determining a refraction of at least an eye of a person under specific spectral conditions.

Said method for determining a refraction of at least an eye of a person under specific spectral conditions may be a method according to the invention comprising an eye illumination step S2, and a refraction determination step S4 as described here.

Said method for determining a refraction of at least an eye of a person under specific spectral conditions may be a method according to the invention comprising a spectral parameter providing step S14, a spectral-refraction model providing step S16 and a refraction determination step S18.

During the resultant refraction determination step S32, for each of the chromatic filters, the refraction resulting of the association of the ophthalmic lens and the chromatic filter is determined.

During the refraction difference determination step S34, a difference between the resultant refraction and the target refraction is determined for each chromatic filter.

During the chromatic filter selection step S36, the chromatic filter inducing the least difference between the resultant refraction and the target refraction is selected.

Advantageously, the selected chromatic filter induces specific spectral conditions which contribute to adapt the refraction to reach a target refraction. Therefore, as the target refraction is not reached solely due to curvature of the ophthalmic lens, the invention allows more flexibility in manufacturing an ophthalmic lens.

As an example, the ametropic shift induced by the filter is used to correct an optical effect. For instance, during the night, a myopic shift may be observed. To compensate this myopic shift, a filter cutting low/medium wavelength may be used. If the prescription for one eye of the person corresponds to +3.00 D with his clear lenses and dark conditions induce a −0.25 D myopic shift, we may propose a new equipment, with a lens having a sphere power of +3.00 D associated to a specific filter cutting low and medium wavelengths, such as a brown filter inducing a shift of +0.25 D, to compensate for the myopic shift. Another application is to adapt a filter to compensate the presbyopia effect. At the beginning of the presbyopia, usually about 45 years old, people usually need eyewear with a small addition, either on single vision or on progressive lenses, to compensate for the loss of accommodation. With this innovation, we propose, alternatively, to adapt a filter, such as on a removable clip adaptable to the frame. The filter may either cut high wavelengths or be a low pass band filter to shift the image on the retina allowing to have the best visual acuity. If the prescription of the wearer includes for example an addition of 1.25 D, we may adapt a low pass band filter, such as a 500 nm pass band, shifting the refraction to −1.25 D at a luminance level of 10 cd/m$^2$. This solution with clips allows to adapt very quickly the best correction with a low price. This application is especially useful in countries with poor visual care access.

Another example, the addition of a filter (low pass band) enables to complete a traditional optical addition by adding this filter for specific near task (precise activities like diy, sewing, computer task) to add a small magnifying power. Seniors or presbyopia people wear addition to compensate presbyopia effect (at distances about 40 cm). For closer distance (specific activity with more attentional concentration), an additional power has to be added. Instead of a new equipment, a specific filter could be added to compensate this additional power. Like in the previous example, adding a low pass band filter enables to compensate the loss of accommodation in near distance. To determine the best filter, either a theoretical model is used as described above or a new refraction determination step is performed in the specific conditions selected by the wearer (working distance, light conditions, . . . ) with different filters in terms of spectrum to determine the suitable filter allowing the lesser accommodation effort. The advantage of using a filter over adapting the lens power, is to keep the original working distance. Indeed, by adding a new optical addition, the wearer would have to bring his working distance closer.

Electronic and electrochromic eyeglasses allow to adapt the power of the lenses but also to filter color of the lenses. Thanks to sensors embedded into the frame, analyzing light conditions, working distance, wearer fatigue (eye lid analysis for example) etc . . . , and from an initial refraction profile of the wearer (refraction, age, pupil behavior, life style, etc.), the optical lens according to the invention adapts the initial refraction by adjusting power and/or adjusting color filter to improve visual performance (visual acuity, contrast, accommodation effort). The choice between power or filter adaptation may be determined, for instance, according to aesthetic criteria, or working distance comfort.

For example, let's consider a person having for both eyes the same prescription under standard spectral conditions of +2.50 D, with the same addition of +2.00. In this example, the person is 50 years old. His favorite activities are: outdoor golfing, laptop activities for his job, and philately on weekends. For golfing, the person wears sunlenses (brown class 3). To maintain an optimal contrast and visual performance for this activity, the ophthalmologist or optician realizes a new refraction determination, under spectral conditions corresponding to a source of a high luminance (above 100 cd/m$^2$) illuminating the chromatic filter of the selected sunlenses. In this example, a shift of +0.25 D is found with a visual acuity increase of 0.05 Log and a 10% improvement of the contrast. The final refraction prescription for his sun equipment may thus be adapted, corresponding to +2.75 D for far distance. For near distance (philately), the person needs a more precise visual performance than what his current progressive lenses provide. In order to improve comfort, the wearer needs a +0.75 D increased addition. In order to solve this issue, the wearer may adapt a filter to maintain an ergonomic distance and also improve the contrast. The proposed filter may be a removable filter, such as a clip, or may correspond to a color configuration of an electrochromic lens. In order to determine the adequate characteristics for the filter, several low pass band filters, having different cutting values, may be tested in order to determine for each filter the corresponding refraction. The filter providing a shift closest to the required shift of, according to this example, +0.75 D would then be selected and provided to the wearer.

Another object of the invention is a system 10 adapted to determine the refraction of at least an eye 2 of a person under specific spectral conditions, the system 10 comprising a light source 4 adapted to illuminate the eye 2 of the person under specific spectral conditions, as illustrated on FIG. 6. The system 10 also comprises a refraction determining device 12 adapted to determine the refraction of the eye 2 of the person.

The specific spectral conditions may be provided by a polychromatic source 6 having a spectrum which is different from the spectrum of a white light and/or by a chromatic filter 8 positioned before the eye 2 of the person.

According to further embodiments of the system according to the invention, the system 10 is adapted to determine the refraction of at least an eye 2 of a person under specific spectral conditions according to a method for determining a refraction of at least an eye of a person under specific spectral conditions according to the invention, the method comprising an eye illumination step S2, and a refraction determination step S4.

Figure 7:
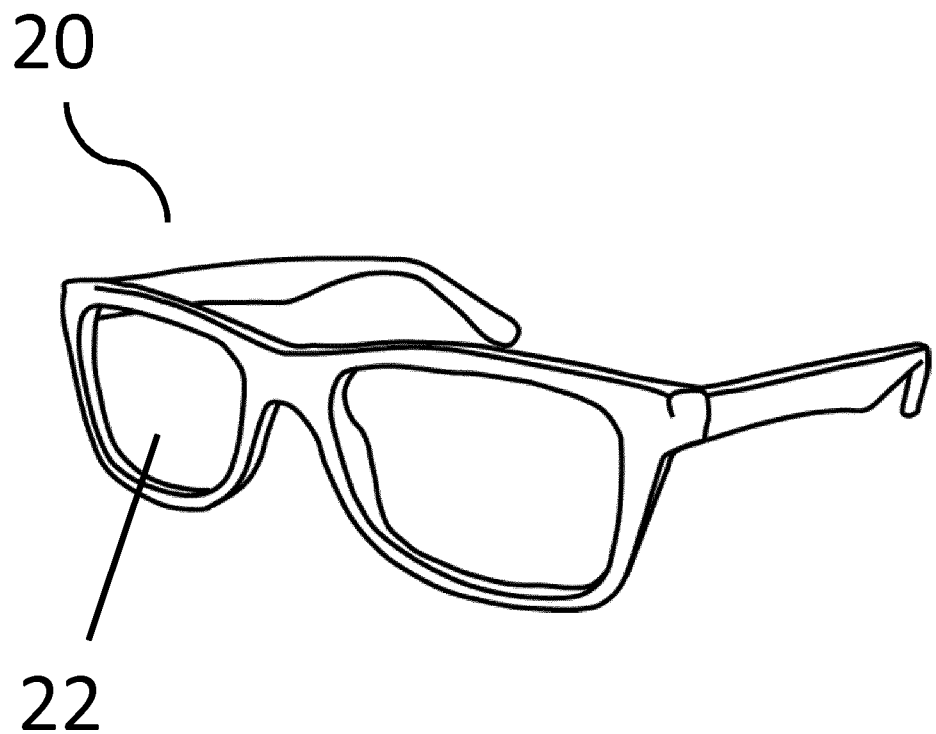
FIG. 7 and FIG. 8 are schematic diagrams of optical systems adapted for a person according to embodiments of the invention.

Another object of the invention is an optical system 20 adapted for a person, as illustrated on FIG. 7, the optical system 20 comprising a component 22 configured so as to refract light before the eye of the person, the optical system 20 being adapted to compensate a refraction of the eye 2 of the person under wearing spectral conditions. The component 22 is chosen as a function of a refraction, and the refraction is determined according to a method for determining a refraction of at least an eye of a person under specific spectral conditions according to the invention.

In embodiments, said method for determining a refraction of at least an eye of a person under specific spectral conditions is a method according to the invention comprising an eye illumination step S2, and a refraction determination step S4.

In embodiments, said method for determining a refraction of at least an eye of a person under specific spectral conditions is a method according to the invention comprising a spectral parameter providing step S14, a spectral-refraction model providing step S16 and a refraction determination step S18.

Figure 8:
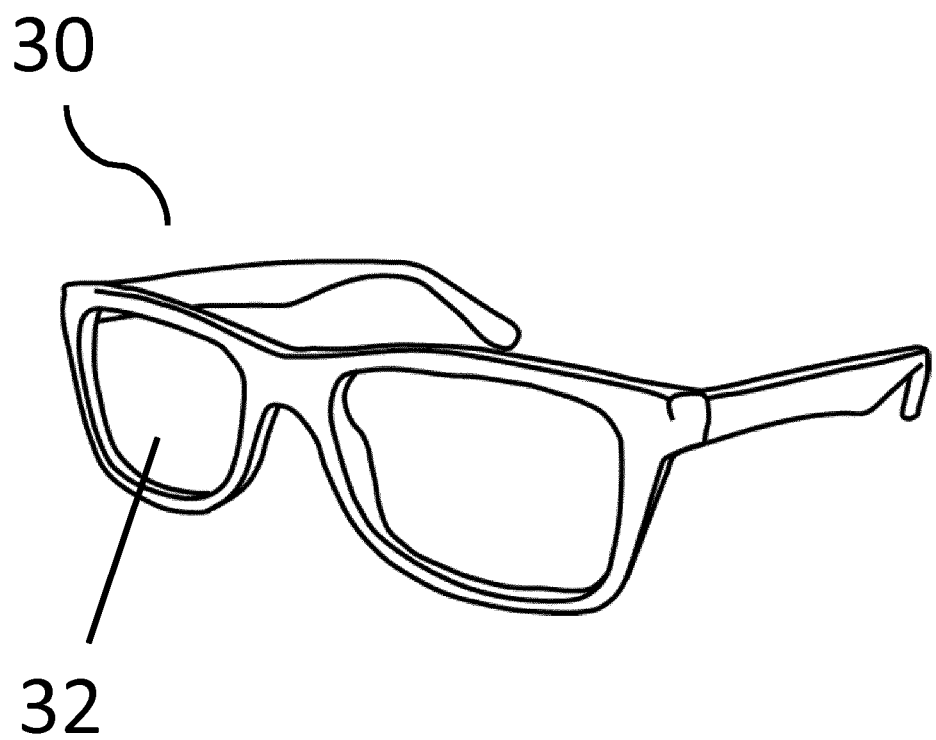

Another object of the invention is an optical system 30 adapted for a person, as illustrated on FIG. 8, the optical system 30 comprising a chromatic filter 32 selected among a plurality of chromatic filters. The chromatic filter 32 is selected according to a method for selecting a chromatic filter for an optical system adapted for a person among a plurality of chromatic filters according to the invention.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. Method for determining a refraction of at least an eye of a person under specific spectral conditions, the method comprising:
   an eye illumination step, during which the eye of the person is illuminated under said specific spectral conditions, said specific spectral conditions being provided by a polychromatic source having a spectrum which is different from the spectrum of a white light source and/or by a chromatic filter positioned before the eye of the person and illuminated by a source, and
   a refraction determination step during which the refraction of the eye of the person is determined under said specific spectral conditions, and
   the refraction determination step comprises measuring the refractive error of the wearer with the specific spectral conditions.

2. The method according to claim 1, wherein the polychromatic source has a spectrum whose at least one chromatic coordinates x or y in the CIE xyY color space differs from the corresponding chromatic coordinates of the black body loci by at least 0.01.

3. The method according to claim 1, wherein the chromatic filter has a chromatic value strictly superior to 10.

4. The method for determining a spectral-refraction model adapted to a person, the method comprising:
   a specific spectral conditions providing step, during which a plurality of specific spectral conditions are provided,
   a spectral parameter providing step, during which for each of the specific spectral conditions, at least one spectral parameter related to said specific spectral conditions is provided,
   a refraction determination step, during which a refraction of the eye of the person is successively determined for each of the specific spectral conditions according to the method of claim 1,
   a spectral-refraction model determining step, during which a model of the refraction of the eye of the person as a function of the spectral parameter is determined based on each of the refractions of the eye of the person and on each of the spectral parameters.

5. The method according to claim 4, wherein during the spectral-refraction model determining step, the model is determined by interpolating and/or extrapolating the refraction of the eye of the person as a function of the spectral parameter.

6. The method for compensating a refraction of an eye of a person under wearing spectral conditions with an optical system comprising a component configured so as to refract light before the eye of the person, the method comprising:
   a refraction determination step according to the method of claim 1 during which a refraction of the eye of the person under specific spectral conditions is determined,
   a optical system providing step, during which an optical system is provided, the optical system comprising a component configured so as to refract light before the eye of the person, the component being chosen as a function of the determined refraction, and
   a refraction compensation step, during which the refraction of the eye of the person under wearing spectral conditions is compensated by the component of the optical system.

7. The method for selecting a chromatic filter for an optical system adapted for a person among a plurality of chromatic filters, the method comprising:
   a target refraction providing step, during which a target refraction is provided,
   a providing step, during which an ophthalmic lens is provided, the ophthalmic lens being associated with a refraction,
   a providing step, during which a plurality of chromatic filters are provided, each chromatic filter being associated with a refraction determined according to the method of claim 1,
   a resultant refraction determination step, during which, for each of the chromatic filter, the refraction resulting of the association of the ophthalmic lens and the chromatic filter is determined, a refraction difference determination step, during which a difference between the resultant refraction and the target refraction is determined for each chromatic filter, and a selection step during which the chromatic filter inducing the least difference between the resultant refraction and the target refraction is selected.

8. The method according to claim 6, wherein the specific spectral conditions are sensibly similar to the wearing spectral conditions.

9. Optical system adapted for a person, the optical system comprising a component configured so as to refract light before the eye of the person, the optical system being adapted to compensate a refraction of the eye of the person under wearing spectral conditions according to the method of claim 6.

10. Optical system adapted for a person, the optical system comprising a chromatic filter selected according to the method of claim 7.

11. The method of claim 1, wherein the polychromatic source has a spectrum whose at least one chromatic coordinates x or y in the CIE xyY color space differs from the corresponding chromatic coordinates of the black body loci by at least 0.02.

12. The method of claim 1, wherein the polychromatic source has a spectrum whose at least one chromatic coordinates x or y in the CIE xyY color space differs from the corresponding chromatic coordinates of the black body loci by at least 0.03.

13. Method according to claim 1, wherein the chromatic filter has a chromatic value strictly superior to 20.

14. Method according to claim 1, wherein the chromatic filter has a chromatic value strictly superior to 30.

15. The method for determining a spectral-refraction model adapted to a person, the method comprising:
- a specific spectral conditions providing step, during which a plurality of specific spectral conditions are provided,
- a spectral parameter providing step, during which for each of the specific spectral conditions, at least one spectral parameter related to said specific spectral conditions is provided,
- a refraction determination step, during which a refraction of the eye of the person is successively determined for each of the specific spectral conditions according to the method of claim 2,
- a spectral-refraction model determining step, during which a model of the refraction of the eye of the person as a function of the spectral parameter is determined based on each of the refractions of the eye of the person and on each of the spectral parameters, and the refraction determination step comprises measuring the refractive error of the wearer with the specific spectral conditions.

16. The method for determining a refraction of at least an eye of a person under specific spectral conditions, comprising:
- a spectral-refraction model providing step, during which a model of a refraction of at least an eye as a function of a spectral parameter is provided,
- a spectral parameter providing step, during which at least one spectral parameter related to specific spectral conditions of the person is provided, and
- a refraction determination step, during which a refraction of the eye of the person under specific light conditions is determined based on the model and on the light parameter, and the refraction determination step comprises measuring the refractive error of the wearer with the specific spectral conditions.

17. The method according to claim 16, wherein the spectral-refraction model is determined according to a method for determining a spectral-refraction model adapted to a person, the method comprising:
- a specific spectral conditions providing step, during which a plurality of specific spectral conditions are provided,
- a spectral parameter providing step, during which for each of the specific spectral conditions, at least one spectral parameter related to said specific spectral conditions is provided,
- a refraction determination step, during which a refraction of the eye of the person is successively determined for each of the specific spectral conditions according to a method for determining a refraction of at least an eye of a person under specific spectral conditions, the method comprising:
  - an eye illumination step, during which the eye of the person is illuminated under said specific spectral conditions, said specific spectral conditions being provided by a polychromatic source having a spectrum which is different from the spectrum of a white light and/or by a chromatic filter positioned before the eye of the person and illuminated by a source, and
  - a refraction determination step during which the refraction of the eye of the person is determined under said specific spectral conditions,
- a spectral-refraction model determining step, during which a model of the refraction of the eye of the person as a function of the spectral parameter is determined based on each of the refractions of the eye of the person and on each of the spectral parameters.

18. The method for compensating a refraction of an eye of a person under wearing spectral conditions with an optical system comprising a component configured so as to refract light before the eye of the person, the method comprising:
- a refraction determination step according to the method of claim 8 during which a refraction of the eye of the person under specific spectral conditions is determined,
- a optical system providing step, during which an optical system is provided, the optical system comprising a component configured so as to refract light before the eye of the person, the component being chosen as a function of the determined refraction, and
- a refraction compensation step, during which the refraction of the eye of the person under wearing spectral conditions is compensated by the component of the optical system.

19. The method for selecting a chromatic filter for an optical system adapted for a person among a plurality of chromatic filters, the method comprising:
- a target refraction providing step, during which a target refraction is provided,
- an ophthalmic lens providing step, during which an ophthalmic lens is provided, the ophthalmic lens being associated with a refraction,
- a chromatic filter providing step, during which a plurality of chromatic filters are provided, each chromatic filter being associated with a refraction determined according to the method of claim 16,
- a resultant refraction determination step, during which, for each of the chromatic filter, the refraction resulting of the association of the ophthalmic lens and the chromatic filter is determined, a refraction difference determination step, during which a difference between the resultant refraction and the target refraction is determined for each chromatic filter, and a chromatic filter selection step during which the chromatic filter inducing the least difference between the resultant refraction and the target refraction is selected.

20. System adapted to determine the refraction of at least an eye of a person under specific spectral conditions, the system comprising:

a light source adapted to illuminate the eye of the person under specific spectral conditions, the specific spectral conditions being provided by a polychromatic source having a spectrum which is different from the spectrum of a white light and/or by a chromatic filter positioned before the eye of the person and illuminated by a source, and a refraction determining device adapted to determine the refraction of the eye of the person, and the refraction determination step comprises measuring the refractive error of the wearer with the specific spectral conditions.

* * * * *